United States Patent [19]

Weissman

[11] Patent Number: 4,600,392
[45] Date of Patent: Jul. 15, 1986

[54] CONTOURED DENTAL POST

[75] Inventor: Bernard Weissman, New York, N.Y.

[73] Assignee: IPCO Corporation, White Plains, N.Y.

[21] Appl. No.: 735,548

[22] Filed: May 20, 1985

[51] Int. Cl.⁴ .............................................. A61C 5/04
[52] U.S. Cl. .................................................... 433/225
[58] Field of Search ............... 433/225, 219, 220, 221, 433/215

[56] References Cited

U.S. PATENT DOCUMENTS

| 347,975 | 8/1886 | Starr | 433/220 |
| 688,661 | 12/1901 | Miller | 433/220 |
| 2,536,669 | 1/1951 | Thau-Jensen | 433/221 |

Primary Examiner—Robert Peshock
Attorney, Agent, or Firm—Goodman & Teitelbaum

[57] ABSTRACT

A contoured dental post for retaining a dental restoration onto a prepared tooth stub, the dental post includes an elongated cylindrical body portion having peripheral grooves for anchoring the body portion within a cement prepared bore in the tooth stub. A pair of radially projecting ribs extends on opposite sides of the body portion, along at least a portion of the length of the body portion. The ribs suitably fit the approximate oval shape of the canal in the tooth stub into which the bore is formed. Preferably, one rib is longer than the other rib. A drill jig is also provided for contouring the canal to receive the dental post. The drill jig includes a stepped head block having a depending shaft extending therefrom for insertion into the bore. A pair of offset apertures is laterally positioned on either side of the shaft and extend through respective stepped portions of the head block and into a portion of the shaft. The distances between the upper surface of the respective stepped portions of the head block and the bottom of the respective apertures position in the shaft there beneath are substantially equal to each other to permit utilization of a single drill bit for drilling out two lateral bores in the canal walls of the tooth stub, whereby the lateral bores have different lengths due to the stepped arrangement of the head block.

15 Claims, 13 Drawing Figures

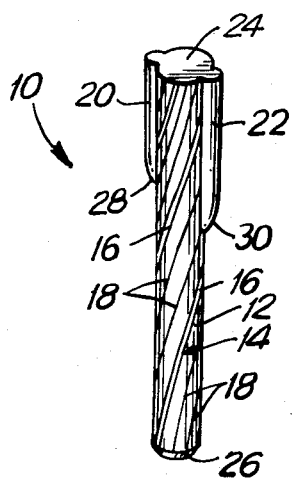
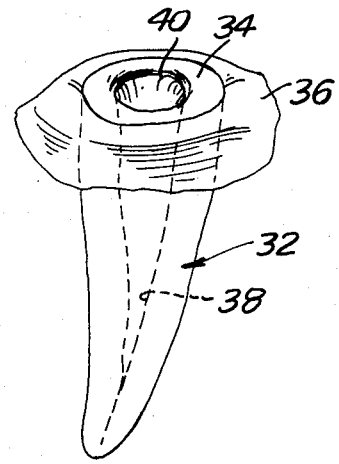
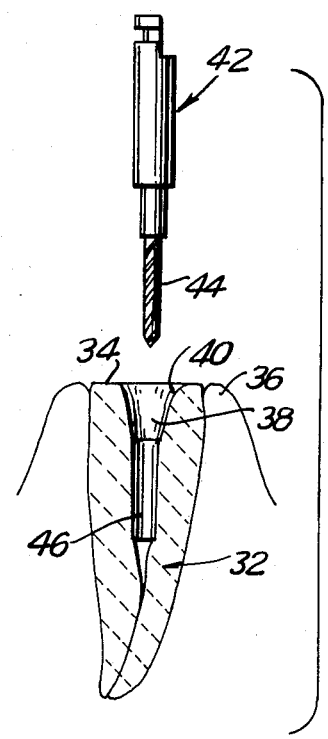
FIG.1  FIG.2  FIG.3
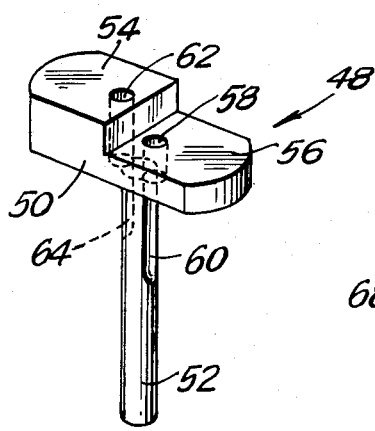
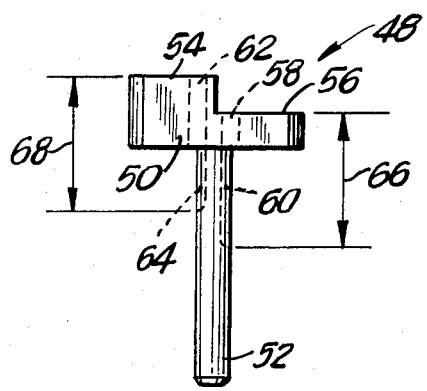
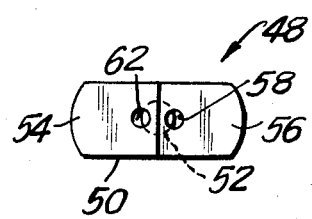
FIG.4  FIG.5  FIG.6

CONTOURED DENTAL POST

BACKGROUND OF THE INVENTION

This invention relates to a dental post system for retaining a dental restoration onto a prepared tooth stub, and more particularly to a contoured dental post which more suitably accommodates the actual shape of the tooth canal in the tooth stub.

In the restoration of devitalized dentition, it is a well known practice to utilize a dental post for retaining a superstructure onto the tooth stub. Typically, the tooth stub is prepared by cutting down the damaged tooth to provide a suitable surface, and then drilling into the apical canal a desired depth to provide an enlarged bore for receiving the dental post. The dental post is then inserted and cemented in the bore. An appropriate core is provided or built up on an upper portion of the dental post, and dental restorative material is used to build a superstructure on the core.

Typically, dental posts heretofore utilized have a generally circular cross section. In preparing the tooth stub to receive such dental posts, circular drill bits are utilized to pre-drill the canal to form a circular bore. The dental posts are then inserted into these bores. However, the actual canal in the tooth stub does not have a circular shape, especially at the upper part thereof, where the canal tends to flare outwardly and often approaches an oval shape.

While it would be possible to drill the canal large enough to encompass the flared upper portion to change the oval shape into a circular shape, this would tend to destroy healthy dentition and weaken the existing tooth stub. As a result, prior art practice has been to drill out the canal using only a size of drill bit adequate enough to receive the dental post. Cement was then inserted into the portions of the canal that were larger than the drilled bore so that the cement filled in the gaps between the inserted dental post and the existing canal shape.

The use of such cement to fill in the disparity between the post and the actual canal shape caused problems after the restoration was built up. The cement has a tendency to loosen, permitting the dental restoration to move with respect to the tooth stub. Such movement permits entry of contaminants and decay between the dental restoration and the tooth stub, and may even cause the dental post to be dislodged from the canal, thus requiring replacement of the restoration.

SUMMARY OF THE INVENTION

Accordingly, it is an object of the present invention to provide a dental post which avoids the aforementioned problems of prior art dental posts.

Another object of the present invention is to provide a dental post which is contoured in order to better approximate the actual shape of the canal in a tooth stub.

A further object of the present invention is to provide a dental post which is contoured to fit the approximate oval cross sectioned shape of the tooth canal and to provide an appropriate jig for drilling the contours in the tooth canal so that such contoured dental post can be received therein.

Yet another object of the present invention is to provide a dental jig for use in providing a contoured bore in a tooth stub upon which a dental restoration is to be built.

Yet a further object of the present invention is to provide a contoured dental post having an interlock arrangement for securing a dental core onto the contoured dental post.

Briefly in accordance with the present invention, there is provided a dental post for retaining a dental restoration onto a prepared tooth stub. The dental post comprises an elongated cylindrical pin provided with means for anchoring the pin within a cement prepared bore in the tooth stub. At least one radially projecting rib extends longitudinally along at least a portion of the length of the pin. The rib is suitable for approximating the oval shape of the canal in the tooth stub into which a bore has been formed for receiving the dental post.

In a preferred embodiment of the present invention, a pair of diametrically opposed radially projecting ribs are provided with one of the ribs being shorter than the other. Preferably, an interlock arrangement is provided for securing a dental core onto the contoured dental post.

The present invention also contemplates a dental drill jig for contouring a drilled bore in the tooth stub into an approximately oval shape in order to accommodate the contoured dental post. The dental jig includes a head block having a stepped configuration. An elongated shaft depends from the center of the head block for insertion into the center of the bore initially drilled into the canal of the tooth stub. A pair of offset apertures are provided through the head block which extend into the shaft along opposing sides thereof. The distance from the top portion of each section of the stepped head to the lower distal end of the offset apertures in the shaft are substantially equal so that a single drill bit can be utilized to drill the two offset holes in the canal on either side of the central bore, wherein one of the holes penetrates further into the tooth stub than the other.

The aforementioned objects, features and advantages of the present invention will, in part, be pointed out with particularity, and will, in part, become obvious from the following more detailed description of the present invention taken in conjunction with the accompanying drawings, which form an integral part thereof.

BRIEF DESCRIPTION OF THE DRAWINGS

In the drawings:

FIG. 1 is a perspective view of the contoured dental post in accordance with the present invention;

FIG. 2 is a perspective view showing a prepared tooth stub prior to the drilling of the contoured bore in its canal;

FIG. 3 is a cross sectional view through the tooth stub of FIG. 2, showing a first step in the formation of the contoured bore;

FIG. 4 is a perspective view of a dental drill jig for use in the formation of the contoured bore to receive the contoured dental post of FIG. 1;

FIG. 5 is a side elevational view of the dental jig shown in FIG. 4;

FIG. 6 is a top view of the dental jig shown in FIG. 4;

In the various figures of the drawings, like reference characters designate like parts.

DESCRIPTION OF THE PREFERRED EMBODIMENTS

Figures 7, 8, 9:
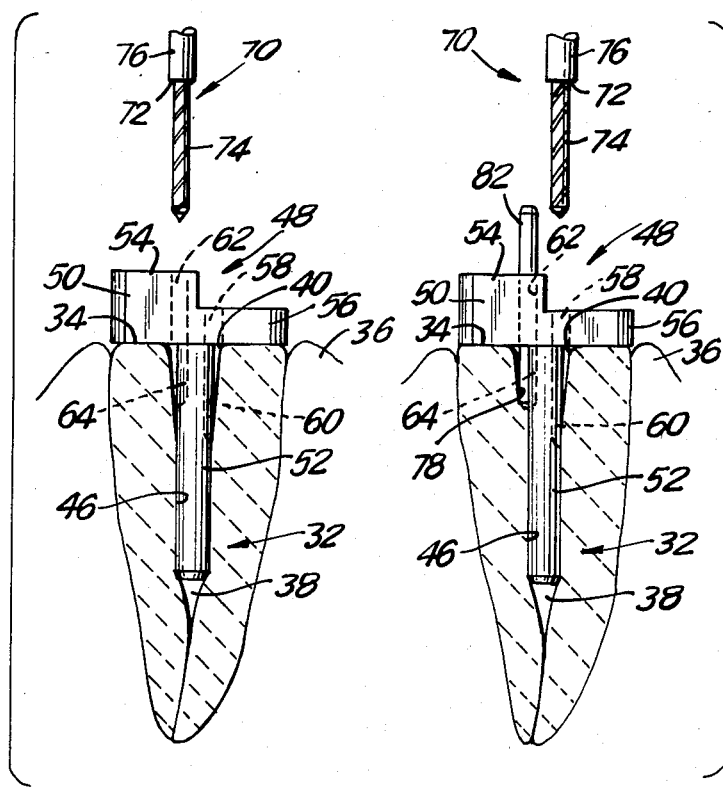
FIG. 7 shows a cross sectional view through the tooth stub similar to FIG. 3, but showing the use of the dental jig of FIG. 4 in a second step in the formation of the contoured bore.
FIG. 8 is a view similar to that shown in Feb. 7, but showing a third step in the formation of the contoured bore.
FIG. 9 is a cross sectional view through the tooth stub showing the contoured bore formed therein.

Referring now to FIG. 1, there is shown a dental post 10 according to the present invention for insertion into a tooth stub upon which a dental restoration will be built up. The dental post 10 includes a substantially cylindrical body portion 12 provided with a plurality of helical grooves 14 for anchoring the dental post 10 in a cement prepared bore provided in the tooth stub.

The anchoring groove means can be of varying types. For example, they can be helical flutes of the type provided in U.S. Pat. No. 4,479,783, issued to the inventor of the present invention. Such flutes are the helical grooves 14 shown in FIG. 1, and include a wider groove 16 separated by a pair of narrower grooves 18. The pitch of the grooves would be greater than the length of the post so as to terminate at the lower end of the post before completing one revolution, thus providing also a vent for insertion of the post into the bore. The anchoring groove means could also be helical threads, as described in U.S. Pat. No. 4,348,183, which also issued to the inventor of the present invention. In such latter case, a vertical channel is included for venting purposes. Accordingly, other types of anchoring arrangements could also be utilized in the present invention.

Laterally projecting on opposite sides of the cylindrical body portion 12, in diametrical opposed relationship, are a pair of projecting ribs 20, 22. Each of the ribs are elongated commencing at a substantially flat top surface 24 of the post 10, and extending longitudinally downwardly along a portion of the length of the body portion 12. Rib 22 extends lower than the rib 20. The combination of the cylindrical body portion 12 in conjunction with the laterally extending ribs 20, 22, provides an approximate oval shape which is more suitably contoured to the actual shape of a canal in a tooth stub, as will hereinafter be described. The lower end of the post 10 is shown champered at 26, with the lower ends of the ribs 20, 22 being rounded at 28, 30, respectively.

The contoured dental post 10 of the present invention will be inserted into a tooth stub 32, shown in FIG. 2, after the tooth stub 32 has been prepared. Initially, tooth stub 32 has first been cut down to provide a prepared upper surface 34 situated within the gum area 36. The apical canal 38 provided in the tooth stub 32 has a substantially oval upper portion 40. The upper portion 40 of the canal 38 is generally rounded and flared at its upper edges.

A first step in the formation of the contoured bore in the tooth stub 32 is to drill into the canal 38 using a conventional drill 42 with an appropriate drill bit 44 to provide a central bore 46 in a manner well known in the dental art. As is well known in the art, drill bits of successively larger sizes will be utilized until the diameter and depth of the bore 46 is appropriate to receive the body portion 12 of the dental post 10.

As will be noted, however, the upper end portion 40 of the canal 38 is flared outwardly and substantially oval in shape. As a result, even though the lower depth of the canal 38 is drilled into a circular shaper defining the bore 46, the upper end portion 40 is wider than the bore 46, and accordingly wider than the body portion 12 of the dental post 10 to be inserted therein. In the past, cement would have been used to fill in the space around the upper portion of the dental post of the prior art to pack the upper end portion 40 so as to tightly secure the prior art dental post. However, such cement would tend to loosen, and the prior art dental post and the restoration thereon would thus move with respect to the tooth stub, which is obviously not desirable as stated above.

As shown in FIGS. 4, 5 and 6, there is provided a dental jig 48 which can be utilized to further drill out the canal and provide a suitably contoured bore shape. The dental jig 48 includes an upper head block 50 from which depends a central cylindrical shaft 52. The head block 50 is stepped, having a thicker portion 54 and a thinner portion 56. A first aperture 58 extends through the thinner portion 56. At least a part 60 of the aperture 58 extends into the shaft 52, as shown by the dotted lines.

A second aperture 62 extends through the thicker portion 54 of the head block 50. At least a part 64 of this aperture 62 also extends into the shaft 52, as shown by the dotted lines. The entire lengths of the apertures 58 and 62 are equal to each other. Specifically, the distance 66 from the top surface of the thinner portion 56 to the bottom of the part 60 of the aperture 58 is the same as the distance 68 from the top surface of the thicker portion 54 to the bottom of the part 64 of the aperture 62. Thus, because of the varying stepped height arrangement of the head block 48, the aperture 58 extends downwardly along the shaft 52 by an additional amount from the aperture 62, this additional amount being equal to the distance between the top surfaces of the thicker portion 54 and the thinner portion 56.

As shown in FIG. 7, the drill jig 48 is mounted on the tooth stub 32 with the shaft 52 being inserted in the bore 46 and the lower surface of the head block 50 being placed on the upper surface 34 of the tooth stub 32. A drill 70 is inserted into one of the apertures, preferably the aperture 62, and is rotated until its shoulder portion 72, between the bit 74 and the shaft 76, reaches the top surface of the thicker portion 54 of the head block 50. In this manner, a short aperture or bore 78 will be drilled into the canal wall of the tooth stub 32 in communication with the bore 46, see FIG. 9. It is noted, that the drill 70 is smaller than the drill 42, the bit 74 of the drill 70 conforming in size to the size of the ribs 20, 22. Furthermore, the bit 74 has a length equal to the entire length of each of the apertures 58 and 62.

With the same drill 70, a second aperture or bore 80 will now be drilled into the canal wall, also in communication with the bore 46, see FIG. 9. Because of the stepped arrangement of the head block 50, the same drill bit 74 can be utilized to drill the two bore 78 and 80, whereby the bore 80 will result in a deeper aperture in the tooth stub 32. As indicated in FIG. 8, the drill 70 is inserted into the other aperture 58, and the shoulder portion 72 of the drill 70 will abut the top surface of the thinner portion 56 to stop the depth of the drilling of the bore 80. Preferably, before drilling the bore 80, a pin 82 is inserted through the aperture 62 into the bore 78 to maintain the drill jig 48 in a fixed position to insure the correct relationship between the bores 78 and 80.

As shown in FIG. 9, after removal of the drill jig 48, a resulting contoured bore 84 is provided in the tooth stub 32, having a substantially cylindrical lower bore 46 with an upper aperture portion including a lateral bore 78 on one side, and a deeper lateral bore 80 on the opposing other side. The bore 88 approximates an over shape at the upper aperture portion thereof, and is in close conformity to the actual shape of the canal 38 of the tooth stub 32.

The particular dental post 10 shown in FIG. 1 can be used for insertion directly into the prepared contoured bore 84 in the tooth stub 32 shown in FIG. 9 and then utilized in any of the well known dental techniques to form a dental core upon which the dental restoration can be built up or mounted in a known manner. Alternately, the dental post can be used with an interlock arrangement to secure the dental core into the dental post, as is described in a co-pending application of the inventor of the present invention.

Figures 10, 11, 12:
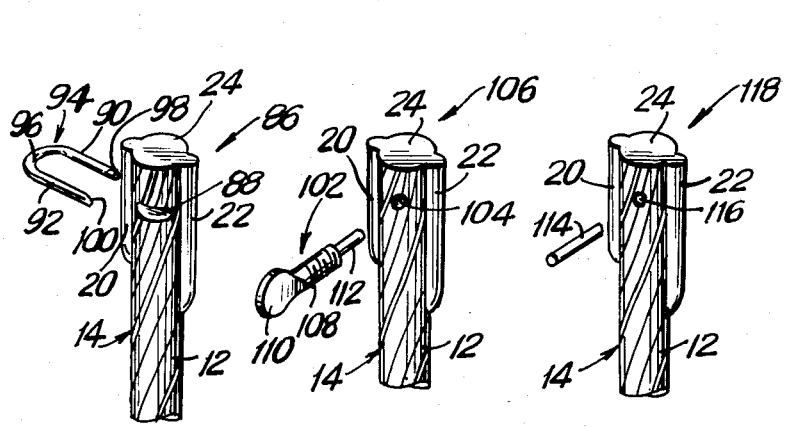
FIG. 10 is an exploded perspective view of the contoured dental post including an interlock arrangement for securing the post to a dental core, utilizing a U-shaped clip.
FIG. 11 is an exploded perspective view of the contoured dental post including an interlock arrangement utilizing a threaded cross pin.
FIG. 12 is an exploded perspective view of the contoured dental post including an interlock arrangement utilizing a locking pin.

Accordingly, as shown in FIG. 10, the dental post 86 is similar to the dental post 10 of FIG. 1, but the modified dental post 86 includes a pair of opposing grooves 88 formed into opposite sides of the periphery of the body portion 12 at an upper end portion thereof. The grooves 88 are used for receiving opposing legs 90, 92 of a U-shaped clip member 94 which can interlock a dental core onto the dental post 86. The clip member 94 includes a bight portion 96 interconnecting the legs 90, 92. The forward free ends of the legs 90, 92 are tapered at 98, 100, respectively.

Figure 13:
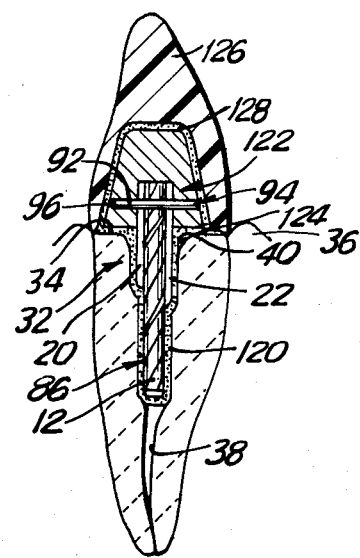
FIG. 13 is a perspective view through the tooth stub, showing insertion of the contoured dental post, the interlocking of the dental core to the post, and the restoration provided on the tooth stub.

As was heretofore described in the aforementioned co-pending application, the clip member 94 can be placed onto the dental post 86 with the legs 90, 92 straddling the body portion 12 and being received in the grooves 88. The grooves 88 are less deep than the thickness of the legs 90, 92, whereby only a portion of the thickness of the legs 90, 92 will be received in the grooves 88. Accordingly, the remaining thickness of the legs will project from the body portion 12 and will be received in the dental core. Thus, after the dental core has been appropriately found of metallic material, it is inserted onto the projecting upper end of the dental post 86 and interlocked onto the dental post 86 by means of the U-shaped clip member 94, as shown in FIG. 13 and explained below.

Other types of interlock arrangements can also be utilized with the contoured post of the present invention. For example, as shown in FIG. 11, there is provided an interlock arrangement including a threaded cross pin 102 which will be at least partially inserted into an aperture 104 extending through the upper end of a modified contoured dental post 106. The dental post 106 is similar to the dental post 10 of FIG. 1 except for the aperture 104. The cross pin 102 includes a substantially threaded cylindrical body portion 108 having a flattened tang portion 110 at one end and a narrow projecting rod 112 at the opposing end thereof.

As heretofore explained in the aforementioned co-pending application, the body portion 108 of the cross pin 102 is threaded into a threaded aperture provided in the dental core by using the tang portion 110 so that the cross pin rod 112 extends into the aperture 104 provided in the upper end of the dental post 106. The dental core will then be securely locked onto the upper end of the dental post 106 and retained in place. The tang portion 110 is then cut off at the outer surface of the dental core.

As shown in FIG. 12, the interlock arrangement includes a locking pin 114 which will be partially received within a detent 116 provided at the upper end of the contoured dental post 118. Here again, the modified dental post 118 is similar to the dental post 10 of FIG. 1 except for the detent 116. The dental core is provided with a suitable aperture for receiving the locking pin 114. The pin 114 will then lock the dental core onto the upper end of the dental post 118.

It is noted, that the dental post can also be cemented into the core, or can be provided with a threaded portion which will thread into the dental core or into a threaded nut to secure the core to the dental post.

As shown in FIG. 13, the contoured dental post 86 is now inserted into the bore 84 in the tooth stub 32. The ribs 20, 22 fit into the drilled lateral bores 78, 80 and the body portion 12 fits in the drilled bore 46 in the tooth stub 32. Appropriate cement 120 is placed into the contoured bore 84 to secure the contoured dental post 86 in the tooth stub 32. A dental core 122 is interlocked onto the contoured dental post 86. The U-shaped clip member 94 as shown in FIG. 10 is utilized to connect the core 122 to the dental post 86. The dental core 122 is secured onto the tooth stub 32 by means of cement 124. Appropriate dental material is used to provide a superstructure 126 which is disposed onto the core 122. Cement 128 is used to retain the superstructure 126 in place on the dental 122.

There has been described heretofore the best embodiment of the invention presently contemplated. However, it is to be understood that various changes and modifications may be made thereto without departing from the spirit of the present invention.

What is claimed is:

1. A dental post for retaining a dental restoration onto a prepared tooth stub having a canal with a bore drilling into the canal walls which have an approximate oval shape adjacent to an outer surface of the tooth stub, said dental post comprising:
   an elongated cylindrical body portion having a substantially uniform circular cross section from a top end to a bottom end of said body portion;
   rib means provided on an upper portion of said body portion for extending into the canal and fitting the approximate oval shape of the canal in the tooth stub, said rib means including a pair of diametrically opposed radially projecting ribs extending from said top end longitudinally along said upper portion of said body portion and being spaced from said bottom end;
   one of said ribs being longer than the other rib to provide pilot means for inserting said ribs into the bore; and
   said body portion including peripheral securing means for anchoring said body portion with cement within the bore in the tooth stub so that a part of said upper portion of said body portion extends above the tooth stub.

2. A dental post as in claim 1, wherein said securing means includes a plurality of externally spaced apart helical flutes longitudinally disposed about said body portion for retaining a lower portion of said body portion within the cement in the bore, and also for providing a vent for said body portion when being inserted into the cement within the bore in the tooth stub.

3. A dental post as in claim 1, wherein said securing means also commences at the top end of said body portion.

4. A dental post as in claim 1, and further comprising interlock means for securement of a dental core onto said dental post, and aperture means provided into an upper part of said cylindrical body portion for receiving at least a part of said interlock means.

5. A dental post for retaining a dental restoration onto a prepared tooth stub having a canal with a bore drilled into the canal walls which have an approximate oval shape adjacent to an outer surface of the tooth stub, said dental post comprising:
   an elongated cylindrical body portion having peripheral securing means along its length for anchoring said body portion with cement within the bore in the tooth stub;
   rib means for extending into the canal and fitting the approximate oval shape of the canal in the tooth stub, said rib means including at least one radially projecting rib extending longitudinally along at least a portion of the length of said body portion;
   interlock means for securement of a dental core onto said dental post;
   aperture means provided into an upper part of said cylindrical body portion for receiving at least a part of said Interlock means;
   said interlock means including a substantially U-shaped clip member having a pair of opposing legs and a bight portion; and
   said aperture means including a pair of lateral grooves disposed in opposing peripheral sides of said upper part of said cylindrical body portion for at least partially receiving a thickness of said legs of said clip member as said legs straddle said cylindrical body portion.

6. A dental post for retaining a dental restoration onto a prepared tooth stub having a canal with a bore drilled into the canal walls which have an approximate oval shape adjacent to an outer surface of the tooth stub, said dental post comprising:
   an elongated cylindrical body portion having peripheral securing means along its length for anchoring said body portion with cement within the bore in the tooth stub;
   rib means for extending into the canal and fitting the approximate oval shape of the canal in the tooth stub, said rib means including at least one radially projecting rib extending longitudinally along at least a portion of the length of said body portion;
   interlock means for securement of a dental core onto said dental post;
   aperture means provided into an upper part of said cylindrical body portion for receiving at least a part of said interlock means;
   said interlock means including an elongated threaded cross pin; and
   said aperture means including an aperture transversely extending through said upper part of said cylindrical body portion for at least partially receiving said cross pin.

7. A dental post for retaining a dental restoration onto a prepared tooth stub having a canal with a bore drifted into the canal walls which have an approximate oval shape adjacent to an outer surface of the tooth stub, said dental post comprising:
   an elongated cylindrical body portion having peripheral securing means along its length for anchoring said body portion with cement within the bore in the tooth stub;
   rib means for extending into the canal and fitting the approximate oval shape of the canal in the tooth stub, said rib means including at least one radially projecting rib extending longitudinally along at least a portion of the length of said body portion;
   interlock means for securement of a dental core onto said dental post;
   aperture means provided into an upper part of said cylindrical body portion for receiving at least a part of said interlock means;
   said interlock means including a locking pin; and said aperture means including a detent provided in said upper part of said cylindrical body portion for at least partially receiving said locking pin.

8. A dental post for retaining a dental restoration onto a prepared tooth stub having a canal with a bore drilled into the canal walls which have an approximate oval shape adjacent to an outer surface of the tooth stub, in combination with a drill jig for contouring the canal walls of the tooth stub to provide the approximate oval shape thereof for receiving said dental post,
   said dental post comprising:
      an elongated cylindrical body portion having peripheral securing means along its length for anchoring said body portion with cement within the bore in the tooth stub; and
      rib means for extending into the canal and fitting the approximate oval shape of the canal in the tooth stub, said rib means including at least one radially projecting rib extending longitudinally along at least a portion of the length of said body portion;
   said drill jig comprising:
      a head block;
      a depending shaft extending from said head block for insertion into the bore; and
      at least one offset aperture passing through said head block and extending longitudinally into a portion of said shaft, said offset aperture being open along said shaft.

9. A dental post in combination with a drill jig as in claim 8, wherein two offset apertures pass through said head block and extend longitudinally into opposing portions of said shaft, both said offset apertures being open along said shaft, and wherein said rib means includes a pair of diametrically opposed radially projecting ribs extending longitudinally along at least a portion of the length of said body portion, whereby said ribs are received in bores which are drilled using said offset apertures.

10. A dental drill jig for contouring a pre-drilled cylindrical bore within a canal of a prepared tooth stub into an approximate oval shape to accommodate a contoured dental post for retaining a dental restoration onto the tooth stub, said drill jig comprising a head block, a depending shaft extending from said head block for insertion into the pre-drilled bore in the tooth stub, and at least one offset aperture passing through said head block and extending into said shaft along a portion of the length thereof, said offset aperture being open along said shaft.

11. A dental drill jig as in claim 10, and further comprising a second offset aperture in diametrick opposition to the first mentioned offset aperture, said second offset aperture also passing through said head block and extending into said shaft along a portion of the length thereof, said second offset aperture also being open along said shaft.

12. A dental drill jig as in claim 11, wherein said second offset aperture extends into said shaft for a shorter length than the first mentioned offset aperture.

13. A dental drill jig as in claim 11, wherein a top portion of said head block is stepped to provide a thinner and thicker portion, said thinner portion of said head block being provided with the first mentioned offset aperture and said thicker portion of said head block being provided with said second offset aperture.

14. A dental drill jig as in claim 13, wherein said offset apertures have lengths equal to each other.

15. A dental drill jig as in claim 10, wherein said head block is of elongated configuration, and said offset aperture is laterally positioned on one side of said shaft, said shaft being centrally positioned on said head block.

* * * * *